United States Patent [19]

Swift

[11] 4,043,177
[45] Aug. 23, 1977

[54] METHOD TO OBSERVE DAMAGE INDUCED IN OPTICAL ELEMENTS BY INTENSE THERMAL RADIATION

[75] Inventor: Roderick D. Swift, Belmont, Mass.

[73] Assignee: The United States of America as represented by the Secretary of the Army, Washington, D.C.

[21] Appl. No.: 679,309

[22] Filed: Apr. 22, 1976

[51] Int. Cl.² .......................................... G01N 25/00
[52] U.S. Cl. ................................. 73/15 R; 356/203
[58] Field of Search ............... 73/15 R; 356/201, 203, 356/239

[56] References Cited

U.S. PATENT DOCUMENTS

| | | | |
|---|---|---|---|
| 2,794,361 | 6/1957 | Shaffer | 356/203 |
| 2,877,683 | 3/1959 | Fischer | 73/15 |
| 3,948,345 | 4/1976 | Rosencwaig | 73/15 |
| B 530,569 | 3/1976 | Milam et al. | 356/239 |

*Primary Examiner*—Herbert Goldstein
*Attorney, Agent, or Firm*—William G. Gapcynski; Lawrence A. Neureither; Charles R. Carter

[57] ABSTRACT

A system by which in situ observations of optical damage induced in optical components by intense thermal radiation may be made. The process includes the determination of the spectral transmission wherein a scanning monochromator is used to illuminate the sample elements with a light beam of monotonically changing wavelength, and the transmitted light is detected and its intensity recorded as a function of wavelength. Optical damage is detected by the resultant changes in the spectral transmission curve.

1 Claim, 1 Drawing Figure

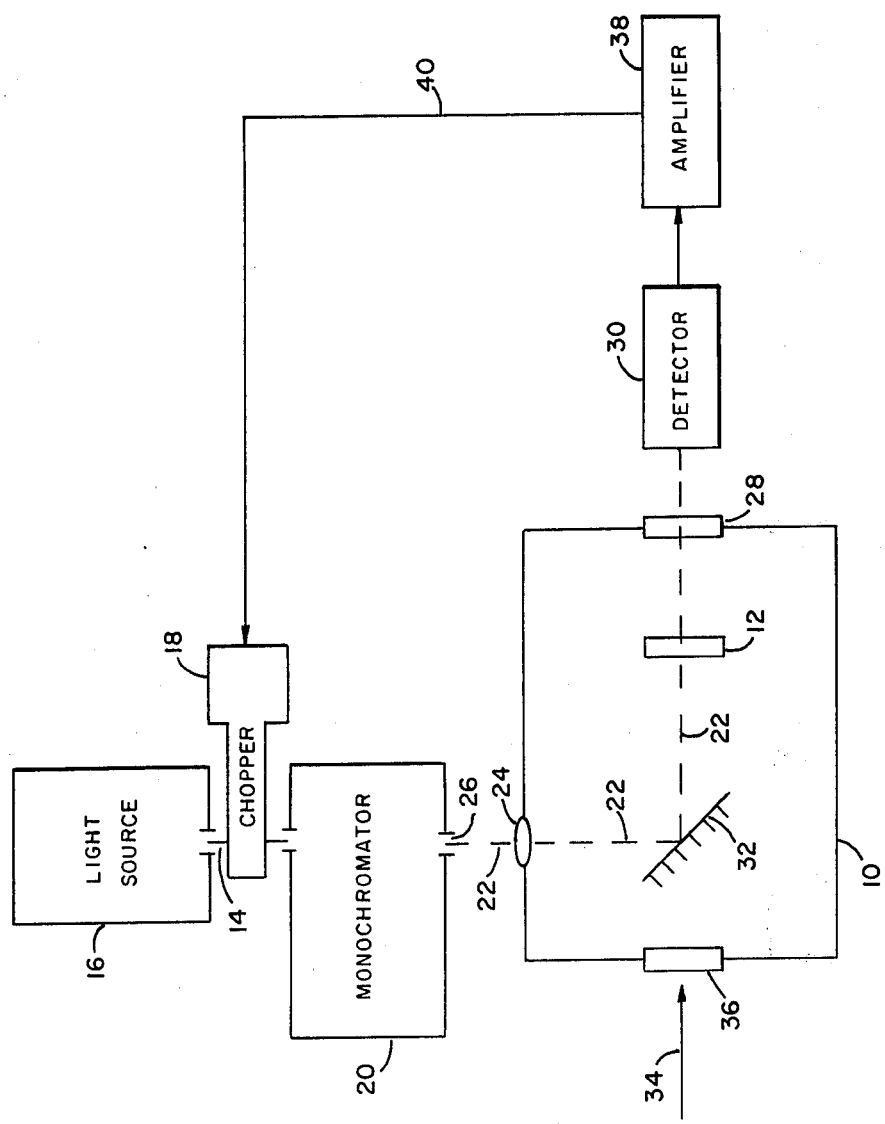

METHOD TO OBSERVE DAMAGE INDUCED IN OPTICAL ELEMENTS BY INTENSE THERMAL RADIATION

DEDICATORY CLAUSE

The invention described herein was made in the course of or under a contract or subcontract thereunder with the Government and may be manufactured, used, and licensed by or for the Government for governmental purposes without the payment to me of any royalties thereon.

BACKGROUND OF THE INVENTION

This invention relates to the field of optical damage detection. No system is known for observing thermal radiation optical damage without removing the suspected elements for testing.

SUMMARY OF THE INVENTION

The present invention has overcome the above state problem by making tests of the optical sample element without removing it from the apparatus within which it was exposed to the thermal radiation. After illuminating an optical sample element with a light beam of monotonically changing wavelength the transmitted light is detected and its intensity recorded as a function of wavelength. The optical element is then exposed to a pulse of thermal radiation. A second spectral transmission scan is made and any optical damage is detected by the resultant changes from the first spectral transmission curve.

This invention may be better understood from the following detailed description taken in conjunction with the accompanying drawing.

BRIEF DESCRIPTION OF THE DRAWING

The single FIGURE shown in the drawing is a diagram showing the basic elements in block form.

DESCRIPTION OF THE PREFERRED EMBODIMENT

Referring now to the drawing reference numeral 10 indicates a test chamber for testing a sample 12. Broadband radiation 14 is emitted from a source 16 and is periodically interrupted by a mechanical chopper 18 and acted upon by a monochromator 20 to form a modulated beam 22 of monochromatic radiation. A lens 24 is used to focus the radiation, emerging from the exit slit 26 of the monochromator, through the optical sample element 12 and a window 28 of the test chamber onto a detector 30. Pivoted mirror 32 serves to fold the optical axis of the beam 22 and is pivoted aside allowing the sample 12 to be exposed to bursts of intense thermal radiation along the path 34 through window 36. A lock-in amplifier 38 is used to process and display the detected signals and is referenced back to chopper 18 by a connection 40. The sample 12 may be moved out of the path of the beam of radiation 22 in order to calibrate the response of the system.

In operation, the monochromator 20 is used to scan the wavelength of the monochromatic beam 22 across the spectral passband of the sample 12. The resultant transmitted radiation is converted to an electronic signal by the detector 30, and amplified, filtered and displayed as a strip-chart recording of a transmission curve. The mirror 32 is then pivoted out of the path 34 of the thermal radiation. Following a thermal radiation pulse, the mirror is replaced into position and the spectral transmission scan is repeated as described above. Any thermally induced changes in the sample 12 may be evidenced by comparing the two transmission curves.

I claim:
1. A process for detecting optical damage induced in optical elements by intense thermal radiation comprising:

projecting a monochromatic light beam onto a movable mirror;

folding the path of said monochromatic light beam onto an optical element, scanning the wavelength of said monochromatic light beam across the spectral bandpass of said optical element;

electrically converting the transmitted radiation into an electronic signal;

amplifying said electronic signal and displaying said signal as a strip-chart recording;

displacing said mirror from its original position;

exposing said optical element to a pulse of intense thermal radiation;

moving said mirror back to its original position;

projecting a monochromatic light beam onto said mirror;

folding the path of said monochromatic light beam onto said optical element scanning the wavelength of said monochromatic light beam across the spectral bandpass of said optical element;

electrically converting the transmitted radiation onto an electronic signal;

amplifying said electronic signal and displaying said signal as a strip-chart recording.

* * * * *